United States Patent
Lee et al.

(10) Patent No.: US 11,643,631 B2
(45) Date of Patent: May 9, 2023

(54) IN VITRO EXPOSURE SYSTEM

(71) Applicants: Electronics and Telecommunications Research Institute, Daejeon (KR); FOUNDATION FOR RESEARCH AND BUSINESS, SEOUL NATIONAL UNIVERSITY OF SCIENCE AND TECHNOLOGY, Seoul (KR)

(72) Inventors: Young Seung Lee, Daegu (KR); Jae-Young Chung, Seoul (KR); Sang Bong Jeon, Daegu (KR)

(73) Assignees: Electronics and Telecommunications Research Institute, Daejeon (KR); FOUNDATION FOR RESEARCH AND BUSINESS, SEOUL NATIONAL UNIVERSITY OF SCIENCE AND TECHNOLOGY, Seoul (KR)

( * ) Notice: Subject to any disclaimer, the term of this patent is extended or adjusted under 35 U.S.C. 154(b) by 1268 days.

(21) Appl. No.: 16/136,019

(22) Filed: Sep. 19, 2018

(65) Prior Publication Data

US 2019/0161721 A1   May 30, 2019

(30) Foreign Application Priority Data

Nov. 29, 2017   (KR) .................. 10-2017-0162054

(51) Int. Cl.
*C12M 1/42*   (2006.01)
*C12M 1/12*   (2006.01)
(Continued)

(52) U.S. Cl.
CPC ............ *C12M 35/06* (2013.01); *C12M 1/12* (2013.01); *C12M 23/34* (2013.01); *C12M 25/02* (2013.01);
(Continued)

(58) Field of Classification Search
CPC ........ C12M 1/12; C12M 23/34; C12M 25/02; C12M 25/04; C12M 35/04; C12M 35/02;
(Continued)

(56) References Cited

U.S. PATENT DOCUMENTS

2010/0159580 A1   6/2010   Kim et al.
2011/0165557 A1   7/2011   Ah et al.
2012/0034596 A1   2/2012   Seidi et al.

FOREIGN PATENT DOCUMENTS

JP   2007222089 A  *  9/2007  ............ C12M 21/02
JP   2007222089 A     9/2007
(Continued)

OTHER PUBLICATIONS

Machine English Translation of JP-2007222089-A (Year: 2007).*
(Continued)

*Primary Examiner* — Michael L Hobbs
*Assistant Examiner* — Lenora A Abel
(74) *Attorney, Agent, or Firm* — William Park & Associates Ltd.

(57) ABSTRACT

Disclosed is an in vitro exposure system that may radiate a uniform field having a constant wavefront to an experimental cell container and expose each cell container to a same electromagnetic field.

9 Claims, 7 Drawing Sheets

(51) Int. Cl.
*C12M 1/00* (2006.01)
*C12M 1/34* (2006.01)
*C12M 1/02* (2006.01)
*G01N 29/24* (2006.01)

(52) U.S. Cl.
CPC ............ *C12M 25/06* (2013.01); *C12M 35/02* (2013.01); *C12M 35/04* (2013.01); *C12M 41/00* (2013.01); *C12M 41/12* (2013.01); *C12M 41/18* (2013.01); *C12M 41/20* (2013.01); *G01N 29/2412* (2013.01); *G01N 2223/101* (2013.01)

(58) Field of Classification Search
CPC ...... C12M 35/06; C12M 41/20; C12M 41/12; C12M 41/18; C12M 41/00; G01N 29/2412; G01N 2223/101
USPC ...................................................... 359/483.01
See application file for complete search history.

(56) References Cited

FOREIGN PATENT DOCUMENTS

| KR | 1020110090508 A | 8/2011 |
| KR | 101116157 B1 | 3/2012 |
| KR | 101354118 B1 | 2/2014 |

OTHER PUBLICATIONS

A Study on the EMF Exposure Control in Smart Society, Assignment No. B0138-16-1002, Dec. 31, 2016, Electronics and Telecommunications Research Institute, South Korea.

Maxim Zhadobov et al., IEEE Transactions on Antennas and Propagation, Evaluation of the Potential Biological Effects of the 60GHz Millimeter Waves Upon Human Cells, Oct. 2009, pp. 2949-2956, vol. 57, Issue 10.

* cited by examiner

IN VITRO EXPOSURE SYSTEM

CROSS-REFERENCE TO RELATED APPLICATION(S)

This application claims the priority benefit of Korean Patent Application No. 10-2017-0162054 filed on Nov. 29, 2017, in the Korean Intellectual Property Office, the disclosure of which is incorporated herein by reference for all purposes.

BACKGROUND

1. Field

One or more example embodiments relate to an in vitro exposure system, and more particularly, to an in vitro exposure system that radiates an electromagnetic field having a uniform wavefront to a broader area of a cell container used for an in vitro experiment.

2. Description of Related Art

An in vitro experiment, which is a basic step to analyze an effect of electromagnetic waves on a human body, may be conducted by exposing each cell container to an electromagnetic field of a constant magnitude and observing effects associated with, for example, an increase in temperature and a mechanism of protein, on the exposed cell container. For such a cell experiment, a cell exposure device configured to generate an electromagnetic field may be used. For the cell exposure device, an electromagnetic field uniformity should be important so that the cell exposure device radiates a uniform electromagnetic field to each of individual cell containers.

An in vitro exposure system may be usually formed in a storage-type structure, such as, for example, a resonance-type waveguide and a transverse electromagnetic (TEM) cell, which is used in the existing low-frequency mobile communication band. Such a storage-type an in vitro exposure system could generate an electromagnetic field in a closed region and thus have an increased exposure efficiency. However, in a short wavelength band such as a millimeter wave for a fifth-generation (5G) communication service, the dimension of such storage-type system should be reduced according to the shorter wavelength and could not store or house a cell container.

Thus, a radiative cell exposure device using an antenna was mainly used in related arts. However, such an existing cell exposure device may be used to observe an exposure effect due to the main beam by arranging a cell container in the main beam direction at the main polarization among angle-based radiation patterns from the antenna.

However, such an existing cell exposure device has limits to a number of containers and a size of area in which the containers are arranged, because the containers are arranged only in the main beam direction of the main polarization to illuminate a uniform electromagnetic field. In addition, the existing cell exposure device may possess larger size due to a distance to a far field region in which the radial dependence of a radiation pattern becomes constant, resulting in its poor exposure efficiency. In general, a wave source such as an antenna generates a spherical wave in a far field region, hence a wavefront may be distorted on both sides of a central axis. And such a wave source may have an additional distortion due to a radiation pattern from the antenna and may not readily illuminate a uniform electromagnetic field to each cell container. Thus, the specific absorption rate of a cell, which is proportional to a square of an electric field, may become sensitive for each cell container.

Therefore, there is a strong need for a exposure system that can overcome such limitations as described above, and generate an electromagnetic field having a uniform wavefront without a distortion for each cell container and perform an in vitro exposure more effectively.

SUMMARY

An aspect provides an in vitro exposure system including an antenna-based chamber-type cell exposure device configured to form a uniform electromagnetic field without a distortion due to a radiation pattern of an electromagnetic field and a wavefront of a spherical wave.

Another aspect also provides an in vitro exposure system including a chamber-type cell exposure device configured to observe a result of a mechanism of a more effective cell experiment based on an increase in experimental cell group and control cell group, by using experimental containers having a same amount of exposure to an electromagnetic field in a broader uniform field area.

According to an example embodiment, there is provided a chamber-type cell exposure device including a uniform field controller configured to radiate an electromagnetic field to a uniform field area formed around a position of a cell container arranged in the chamber-type cell exposure device, a temperature sensor configured to sense an internal temperature of the chamber-type cell exposure device that increases by the electromagnetic field radiated to the uniform field area, an air-cooling ventilation controller configured to control an air flow by adjusting an internal ventilation speed of the chamber-type cell exposure device based on the internal temperature sensed by the temperature sensor, a detachable support configured to adjust a position of the cell container to be arranged in the uniform field area, a planar scan probe configured to monitor a flatness and an exposure efficiency of the electromagnetic field radiated from the uniform field controller based on an amount of the electromagnetic field exposed to the uniform field area, and a position controller configured to control a position of the planar scan probe.

The uniform field controller may include an antenna configured to radiate the electromagnetic field, and at least one lens configured to form a wavefront of the electromagnetic field.

The uniform field controller may radiate the electromagnetic field to the uniform field area using the flatness determined by a strength of the electromagnetic field in the uniform field area in which the cell container is arranged and by a phase of a wavefront of the electromagnetic field.

The cell container may have an electromagnetic field absorptance that varies based on a direction of the electromagnetic field radiated from the uniform field controller.

The detachable support may be at a height adjusted to allow the cell container to be arranged in an area with an identical exposure intensity and an identical phase of the electromagnetic field based on a uniformity of the electromagnetic field in the uniform field area.

The detachable support may be provided in a form that prevents a scattering distortion of the electromagnetic field radiated from the uniform field controller.

The planar scan probe may be arranged in the chamber-type cell exposure device in a direction that is 90 degrees (°)

of rotation different from a main polarized direction of the electromagnetic field radiated from the uniform field controller.

The planar scan probe may measure a distortion of the electromagnetic field by a signal reflected from a wave absorber of the chamber-type cell exposure device at a position at which the planar scan probe is arranged in the chamber-type cell exposure device, and measure the amount of the electromagnetic field exposed based on the measured distortion of the electromagnetic field.

The planar scan probe may determine a characteristic of a wavefront of the electromagnetic field with an identical exposure intensity and an identical phase of the electromagnetic field based on the flatness and the exposure efficiency of the electromagnetic field.

According to another example embodiment, there is provided an in vitro exposure system including a signal generation device configured to generate an electromagnetic field to be radiated to a cell container, a power monitoring device configured to monitor power of the electromagnetic field, a chamber-type cell exposure device configured to radiate the electromagnetic field to a uniform field area formed around a position at which at least one cell container is arranged and expose each of the cell container to the same electromagnetic field, and a control device configured to control an operation of the chamber-type cell exposure device.

The signal generation device may include a signal generator configured to generate the electromagnetic field, a power amplifier configured to amplify the generated electromagnetic field, an isolator configured to perform filtering on an electromagnetic field amplified by the power amplifier, a directional coupler configured to measure a reflection level of a reflected signal of the electromagnetic field amplified by the power amplifier and determine a threshold value of the measured reflection level, and an adaptor configured to feed, to the chamber-type cell exposure device, the electromagnetic field obtained through the filtering performed by the isolator.

The power monitoring device may include a power sensor configured to sense power at a reflection level determined from the signal generation device, and a power meter configured to measure power of the electromagnetic field measured from the chamber-type cell exposure device.

The chamber-type cell exposure device may include a uniform field controller configured to radiate the electromagnetic field to the uniform field area formed around the position of the cell container arranged in the chamber-type cell exposure device, a temperature sensor configured to sense an internal temperature of the chamber-type cell exposure device that increases by the electromagnetic field radiated to the uniform field area, an air-cooling ventilation controller configured to control an air flow by adjusting an internal ventilation speed of the chamber-type cell exposure device based on the internal temperature sensed by the temperature sensor, a detachable support configured to adjust a position of the cell container to be arranged in the uniform field area, a planar scan probe configured to monitor a flatness and an exposure efficiency of the electromagnetic field radiated from the uniform field controller based on an amount of the electromagnetic field exposed to the uniform field area, and a position controller configured to control a position of the planar scan probe.

The uniform field controller may radiate the electromagnetic field to the uniform field area using the flatness determined by a strength of the electromagnetic field and a phase of a wavefront of the electromagnetic field in the uniform field area in which the cell container is arranged.

The detachable support may be at a height adjusted to allow the cell container to be arranged in an area with an identical exposure intensity and an identical phase of the electromagnetic field based on a uniformity of the electromagnetic field in the uniform field area.

The detachable support may be provided in a form that prevents a scattering to distortion of the electromagnetic field radiated from the uniform field controller.

The planar scan probe may be arranged in the chamber-type cell exposure device in a direction that is 90 degrees (°) of rotation different from a main polarized direction of the electromagnetic field radiated from the uniform field controller.

The planar scan probe may measure a distortion of the electromagnetic field by a signal reflected from a wave absorber of the chamber-type cell exposure device at a position at which the planar scan probe is arranged in the chamber-type cell exposure device, and measure the amount of the electromagnetic field exposed based on the measured distortion of the electromagnetic field.

The planar scan probe may determine a characteristic of a wavefront of the electromagnetic field with an identical exposure intensity and an identical phase of the electromagnetic field based on the flatness and the exposure efficiency of the electromagnetic field.

The control device may include a system controller configured to adjust an internal temperature of the chamber-type cell exposure device, a measurement controller configured to control a position of the planar scan probe at which the cell container is to be arranged in the chamber-type cell exposure device, and a spectrum analyzer configured to measure a strength of the electromagnetic field radiated inside the chamber-type cell exposure device through the planar scan probe.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, operations, elements, and/or components, but do not preclude the presence or addition of one or more other features, integers, operations, elements, components, and/or groups thereof.

Terms such as first, second, A, B, (a), (b), and the like may be used herein to describe components. Each of these terminologies is not used to define an essence, order, or sequence of a corresponding component but used merely to distinguish the corresponding component from other component(s). For example, a first component may be referred to as a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing.

Unless otherwise defined, all terms, including technical and scientific terms, used herein have the same meaning as commonly understood by one of ordinary skill in the art to which this disclosure pertains based on an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings.

Figure 1:
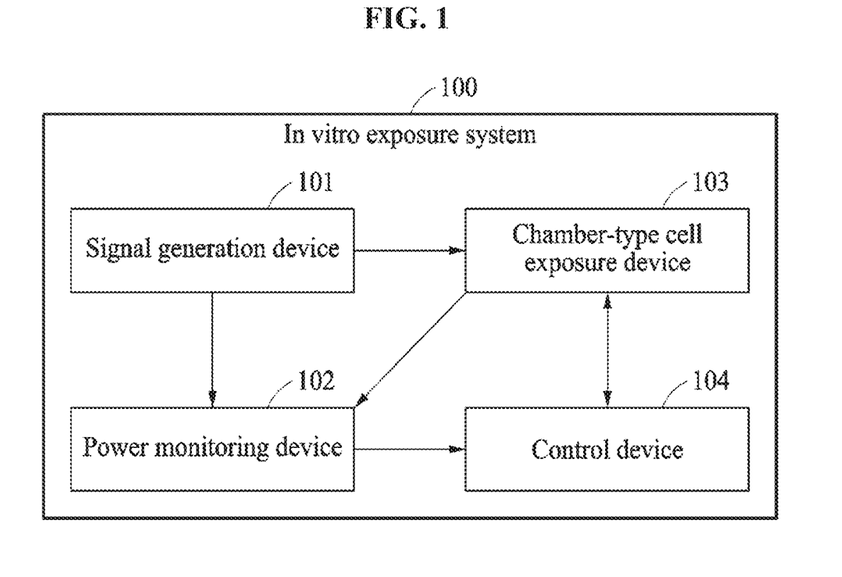
FIG. 1 is a diagram illustrating an example of an in vitro exposure system according to an example embodiment.

FIG. 1 is a diagram illustrating an example of an in vitro exposure system according to an example embodiment.

Referring to FIG. 1, an in vitro exposure system 100 may perform a method that may enable a more effective cell experiment using an antenna-based chamber-type cell exposure device 103 including a uniform field controller. Provided herein is the chamber-type cell exposure device 103 that may radiate a uniform field with a constant wavefront to an experimental cell container and expose each cell container to a same electromagnetic field, thereby enabling a more effective cell experiment in a broader area.

The in vitro exposure system 100 includes a signal generation device 101, a power monitoring device 102, the chamber-type cell exposure device 103, and a control device 104.

The signal generation device 101 may generate an electromagnetic field in a short wavelength such as a millimeter wave band to radiate the generated electromagnetic field to a cell container used for a cell experiment.

The power monitoring device 102 may receive power for the electromagnetic field generated by the signal generation device 101, and verify whether the in vitro exposure system 100 operates normally and whether a desired level of power is generated for an operation of the chamber-type cell exposure device 103

The chamber-type cell exposure device 103 may radiate the electromagnetic field to a uniform field area formed around a position at which at least one cell container is arranged, and exposure each cell container to the same electromagnetic field.

The control device 104 may control the operation of the chamber-type cell exposure device 103.

Using such components described above, it is possible to generate a uniform field with a constant flatness to be radiated to a specific uniform field area in the chamber-type cell exposure device 103, and thus to radiate a same electromagnetic field to individual cell containers. Thus, it is possible to reduce a size of the chamber-type cell exposure device 103, compared to an existing far field-type exposure device, and increase an exposure efficiency and reduce a sensitivity of an electromagnetic wave absorptance for each cell container.

In addition, it is possible to arrange a cell container including an experimental subject in a broader area, and thus to increase an experimental efficiency based on an increase in the number of experimental groups and control groups. Further, by adding components such as an air-cooling ventilation controller configured to maintain a temperature of the chamber-type cell exposure device 103 and a scan probe configured to inspect or check a uniform field area, it is possible to perform cell exposure in an optimal environment. For example, using a planar scan probe, it is possible to inspect or check a distortion level of a reflected signal internally generated in the chamber-type cell exposure device 103, and evaluate a characteristic of an electromagnetic field of the in vitro exposure system 100.

According to an example embodiment, it is possible to increase an experimental efficiency based on an increase in experimental cell groups and control cell groups by radiating an electromagnetic field to a greater size of a uniform field area in a chamber-type cell exposure device. In addition, it is also possible to provide an in vitro exposure system that may be reduced in size, and have an improved exposure efficiency and a reduced sensitivity of an electromagnetic wave absorptance for each cell container.

According to an example embodiment, it is possible to effectively conduct an experiment in an optimal environment using system components, such as, for example, a planar scan probe used to determine a uniform field area and a reflection level and evaluate characteristics of an electromagnetic field, an automatic height adjusting support used to radiate an electromagnetic field at a position with an optimal uniformity, and a detachable support used to maintain a uniformity of a radial electromagnetic field and inspect or check the uniformity.

Figure 2:
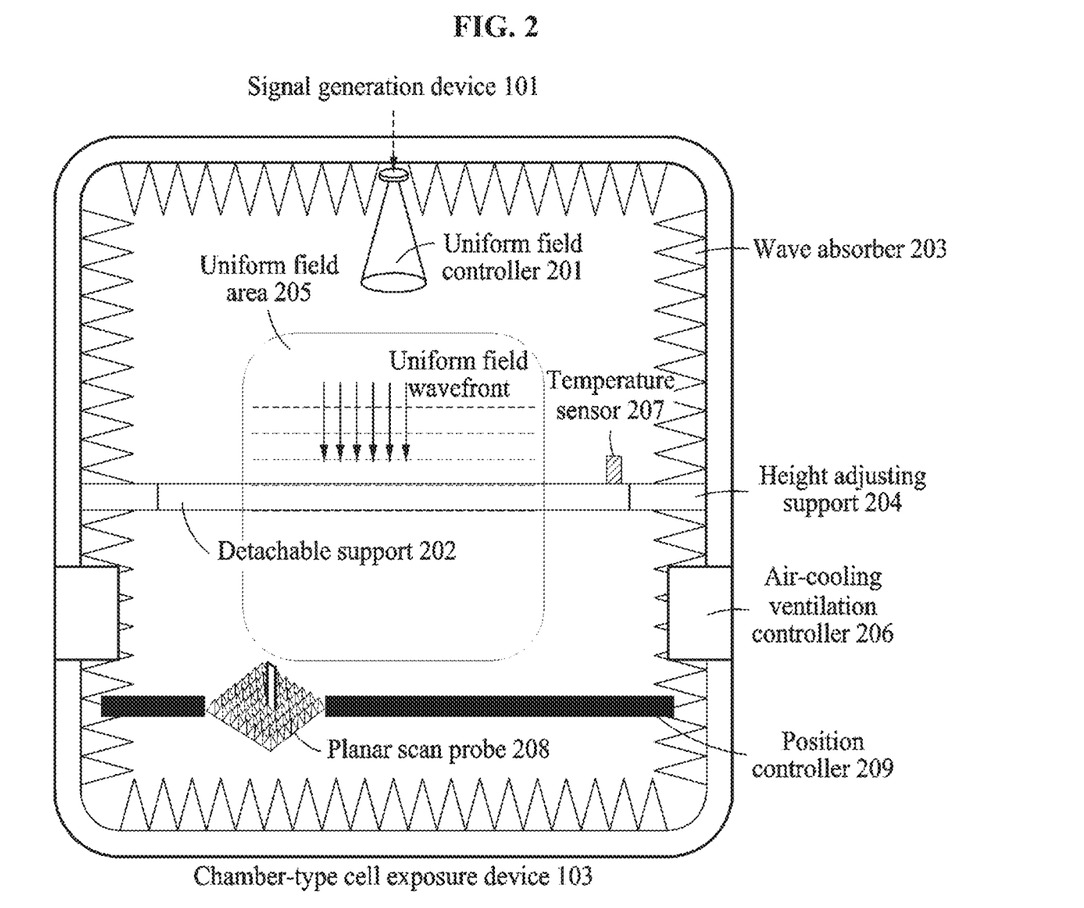
FIG. 2 is a diagram illustrating an example of a chamber-type cell exposure device according to an example embodiment.

FIG. 2 is a diagram illustrating an example of a chamber-type cell exposure device according to an example embodiment.

Referring to FIG. 2, the chamber-type cell exposure device 103 may radiate an electromagnetic field having a constant wavefront to a broader area of a cell container used for a cell experiment. The chamber-type cell exposure device 103 includes a uniform field controller 201, a temperature sensor 207, an air-cooling ventilation controller 206, a detachable support 202, a planar scan probe 208, and a position controller 209.

The uniform field controller 201 may radiate an electromagnetic field fed from the signal generation device 101 to a specific area of the chamber-type cell exposure device 103. The radiated electromagnetic field may generate a uniform field in the specific area of the chamber-type cell exposure device 103. Herein, this specific area in which the uniform field is formed is referred to as a uniform field area 205. In the uniform field area 205, a uniform field wavefront may be formed by the electromagnetic field radiated through the uniform field controller 201.

Herein, the electromagnetic field fed to the uniform field controller 201 may have a power level which may be determined based on a power density of the electromagnetic field radiated into the uniform field area 205 having a constant flatness and on an exposure efficiency by the uniform field controller 201.

The temperature sensor 207 may determine whether a temperature required for experimental cell exposure is optimal, for example, at 37 degrees Celsius (° C.), and detect whether an internal temperature of the chamber-type cell exposure device 103 increases due to the irradiation of the electromagnetic field. In addition, the temperature sensor 207 may transfer, to a system controller of the control device 104, the detected internal temperature of the chamber-type cell exposure device 103.

The air-cooling ventilation controller 206 may interwork with the system controller of the control device 104 based on a temperature measured by the temperature sensor 207, and adjust a ventilation speed indicated by unit of revolutions per minute (RPM) based on whether the temperature increases or not to prevent an increase in temperature. The air-cooling ventilation controller 206 may be embodied in a structure such as, for example, a honeycomb, to shield the electromagnetic field, and provided in a lower end portion of the detachable support 202 to reduce an influence of an air flow by an air-conditioning system on a cell experiment.

The detachable support 202 may be formed of a light material such as Styrofoam having a relative dielectric permittivity close to 1 to prevent a scattering distortion effect of the radiated electromagnetic field, and such a material may facilitate handing of the detachable support 202 in the chamber-type cell exposure device 103. In addition, the detachable support 202 may be detachable as needed, when the planar scan probe 208 operates in an inspection mode. Thus, the detachable support 202 may be at an adjustable height to allow the cell container to be arranged in an area with an identical exposure intensity and an identical phase of the electromagnetic field based on an electromagnetic field uniformity in the uniform field area 205. In addition, the detachable support 202 may also be at an adjustable height by interworking with a height adjusting support 204.

The height adjusting support 204 may be a component provided on a wall of the chamber-type cell exposure device 103 to support the detachable support 202, and designed such that a structure thereof fits a structure of the detachable support 202. Through such a design of the structures, the detachable support 202 may be at an adjustable height, enabling a cell container used for cell exposure to be at a position having an optimal uniformity in the uniform field area 205, unlike an existing design through which a position of the cell container is fixed in an existing far field main beam exposure device.

The planar scan probe 208 may be a component configured to measure an electric field value from a cross-sectional plane, and verify whether the uniform field controller 201 desirably generates a uniform field with a required flatness and exposure efficiency in a uniform field inspection mode. Herein, in the uniform field inspection mode, a test or an inspection may be performed after the detachable support 202 is detached.

The planar scan probe 208 may be rotated to face a direction that is different from a main polarized wave direction of the uniform field controller 201, for example, a side surface portion or a lower end portion of the chamber-type cell exposure device 103. Thus, the planar scan probe 208 may verify whether a distortion of the uniform field by a signal reflected from a wave absorber 203 relative to a desired main radiated signal is less than or equal to a predetermined value, for example, whether a reflection level is less than −60 decibels (dB). The wave absorber 203 may be a portion that is formed of a metal material to shield the electromagnetic field from being escaped externally and used to absorb the radiated electromagnetic field to reduce an amount of the electromagnetic field reflected from an outer wall of the chamber-type cell exposure device 103.

The planar scan probe 208 may inspect or verify an electromagnetic field performance of the in vitro exposure system 100 including the chamber-type cell exposure device 103 from which the uniform field controller 201 is excluded. Herein, when the reflection level exceeds the predetermined value, the exceeding reflection level may indicate that the chamber-type cell exposure device 103 may need to be improved overall. For details, reference may be made to a low-reflection zone, or a quiet zone, of an antenna measurement chamber.

In addition, since an additional area may need to be provided in a lower end portion of the uniform field area 205 to reduce a reflected signal level, that a size of an exposure-type chamber does not increase due to the installation of the planar scan probe 208 may be a characteristic of the in vitro exposure system 100 including the chamber-type cell exposure device 103. In the inspection mode, measured values obtained by the planar scan probe 208 may be input to and indicated by a spectrum analyzer of the control device 104, and be also indicated by the system controller of the control device 104 through a measurement controller of the control device 104.

In addition, the planar scan probe 208 may perform measurement by being rotated by 90 degrees (°) from its original position, and may thus perform a test on a cross-polarization discrimination (XPD), or a level of a cross-polarization component that is not necessary, in addition to intrinsic co-polarization that is necessary for cell exposure. Further, the planar scan probe 208 may also be used to measure and inspect transfer power of the electromagnetic field radiated from the uniform field controller 201 in a general experimental cell exposure mode. The measured power may be transferred to and indicated by a power meter of the power monitoring device 102, and be simultaneously transferred to and indicated by the system controller of the control device 104. The planar scan probe 208 may contribute to an overall simplification of the in vitro exposure system 100) without an additional sensing device to measure and inspect an amount of the electromagnetic field exposed by the cell exposure.

The position controller 209 may be a positioner configured to move the planar scan probe 208 to a desired position for measurement, and triaxially move the planar scan probe 208 with respect to a width axis, a length axis, and a height axis and rotate the planar scan probe 208 such that an end of the planar scan probe 208 faces another direction. In addition, the position controller 209 may have a positional accuracy of ¼ or less of an exposure wavelength to determine a characteristic of an observed wavefront. A movement of the position controller 209 may be controlled to control a position of the planar scan probe 208 through a control signal transferred from the measurement controller of the control device 104.

Figure 3:
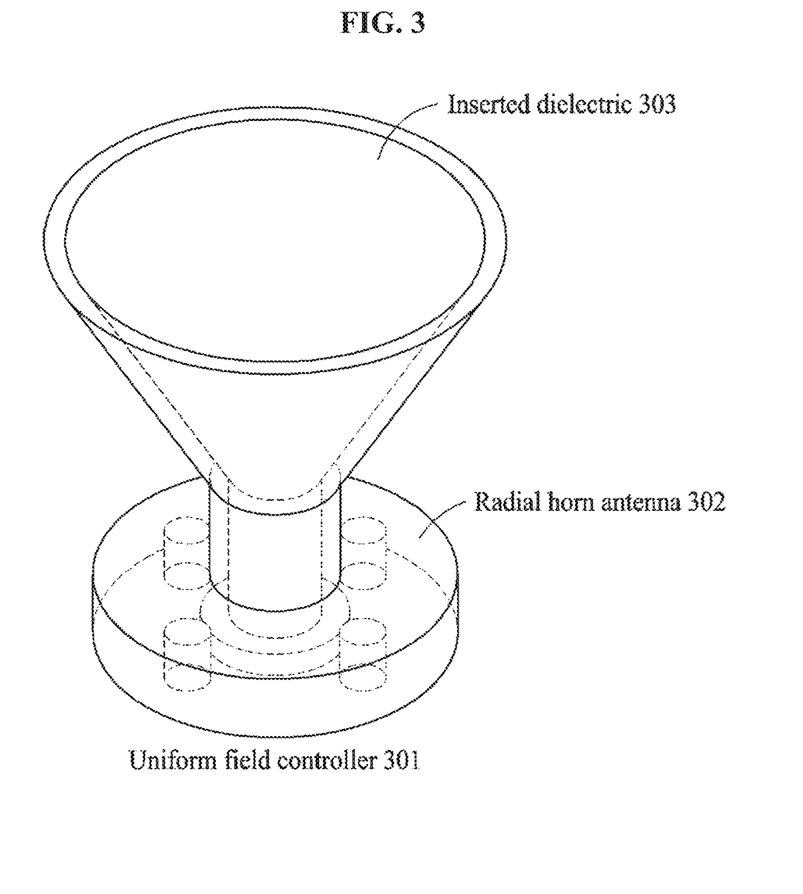
FIG. 3 is a perspective view of an example of a uniform field controller using an inserted dielectric and a radial horn antenna according to an example embodiment.

FIG. 3 is a perspective view of an example of a uniform field controller using an inserted dielectric and a radial horn antenna according to an example embodiment.

Referring to FIG. 3, a uniform field controller 301 may radiate an electromagnetic field to a uniform field area formed around a cell container arranged in a chamber-type cell exposure device. The uniform field controller 301 includes an antenna, or hereinafter a radial horn antenna 302, and one or more lens forming a wavefront of the electromagnetic field. When the radial horn antenna 302 and the lens are arranged separately from one another in a space in the chamber-type cell exposure device, a sensitivity may increase due to a focal length of the lens, and thus obtaining a design parameter of the chamber-type cell exposure device may not be easy and an additional space may be needed for the arrangement in the chamber-type cell exposure device.

Thus, according to an example embodiment, the uniform field controller 301 may be used to resolve such issues related to the design parameter and the additional space. For example, as illustrated, the uniform field controller 301 may be provided in a single integrated structure in which a dielectric medium, for example, an inserted dielectric 303, having a lens effect is inserted in the radial horn antenna 302. Through such a structure, the uniform field controller 301 may be effectively provided inside the chamber-type cell exposure device. In addition, when radiating the electromagnetic field to a space in the chamber-type cell exposure device, the uniform field controller 301 may generate the electromagnetic field having a uniform wavefront through the radial horn antenna 302 generating a distortion of an overall wavefront.

The cell container may be arranged in the chamber-type cell exposure device, and may absorb the electromagnetic field radiated through the radial horn antenna 302 of the uniform field controller 301. Herein, an electromagnetic wave absorptance of the cell container may vary based on a direction of the electromagnetic field radiated through the uniform field controller 301. Herein, in a short wavelength band such as a millimeter wave, the radial horn antenna 302 configured to fix a polarized wave of the electromagnetic field radiated from the uniform field controller 301 to one side and having a symmetrical radiation pattern may be used as a main component for radiation.

Thus, the uniform field controller 301 may radiate the electromagnetic field to the uniform field area in which the cell container is arranged, using a flatness that may be determined by a strength of the electromagnetic field and a phase of a wavefront of the electromagnetic field. Thus, according to an example embodiment, it is possible to observe the strength of the electromagnetic field and the phase of the wavefront from an observation position at which the cell container is arranged in the chamber-type cell exposure device, or the uniform field area.

The flatness of the electromagnetic field may be defined using a mean value and a deviation between a maximum value and a minimum value of the observed strength and the observed phase of the wavefront phase. That is, the flatness may be defined such that the electromagnetic field is radiated into a specific range of the uniform field area in the chamber-type cell exposure device, using the uniform field controller 301. Herein, the specific range may be a section in the uniform field area into which the electromagnetic field having the uniform wavefront is radiated. For example, the flatness may be defined to satisfy a condition for the strength of the electromagnetic field being less than 0.5 dB (<0.5 dB) and a planar phase being less than ±20 (<±20). The defined flatness may be represented by Equation 1.

$$\eta_e = \frac{1}{P_{rad}} \int \int_A P_D dA \qquad \text{[Equation 1]}$$

Referring to Equation 1 above, all measurements or values to be measured may be optimized using an electromagnetic field exposure efficiency. In Equation 1, $\eta_e$ denotes an electromagnetic field exposure efficiency. $P_{rad}$ denotes a total radiation power that is radiated from the uniform field controller 301, and $P_D$ denotes a radiated power density at a point at which the cell container is positioned. A denotes a cross-sectional area at which the cell container is positioned.

For example, when the radiated power density $P_D$ required for a cell experiment is determined, the exposure efficiency $\eta_e$ may be determined from the total radiation power $P_{rad}$ fed from the signal generation device 101. Final values of the strength and the phase of the electromagnetic field radiated to the uniform field area may be determined by setting a weight required for each observed flatness value of the strength and the phase of the electromagnetic field and optimizing values. Herein, the weight may not exceed a value of 1, with the two variables—the strength and the phase of the electromagnetic field—combined. In addition, when the exposure efficiency $\eta_e$ is set to be an unknown quantity as an optimization variable, the weight may be optimized not to exceed a value of 1, with three variables—the strength and the phase of the electromagnetic field, and the exposure efficiency $\eta_e$—combined.

Figure 4:
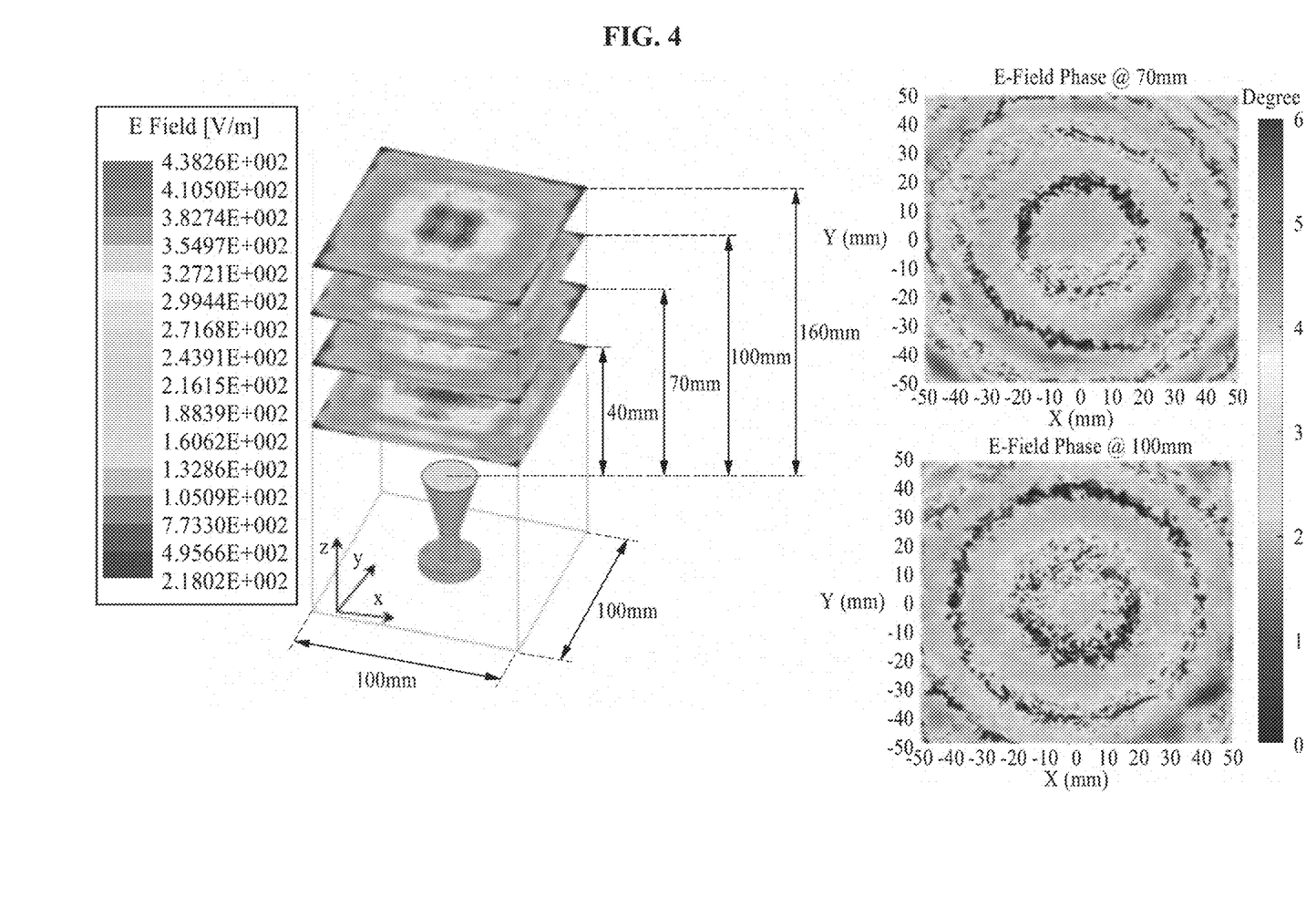
FIG. 4 is a diagram illustrating an example of an observed plane of a wavefront in a uniform field area, and an example of a uniformity in electromagnetic field strength and phase according to an example embodiment.

FIG. 4 is a diagram illustrating an example of an observed plane set in a uniform field area in which a cell container is to be arranged based on a wavefront in a form of a plane wave, and an example of a phase uniformity of an electromagnetic field observed from the plane according to an example embodiment. Referring to FIG. 4 it is verified that a planar phase has a variation range of less than ±2° (<±2°) based on 3° and satisfies a uniform field condition.

Referring to FIG. 4, a uniform field controller may radiate an electromagnetic field to a uniform field area of a chamber-type cell exposure device. Herein, the uniform field controller may radiate the electromagnetic field that has a same wavefront corresponding to a distance from a point at which a radial horn antenna is disposed to the uniform field area. The electromagnetic field radiated to the uniform field area may be exhibited differently from a general antenna radiation pattern on a remote in-phase spherical surface based on an azimuth and an elevation angle.

Figure 5:
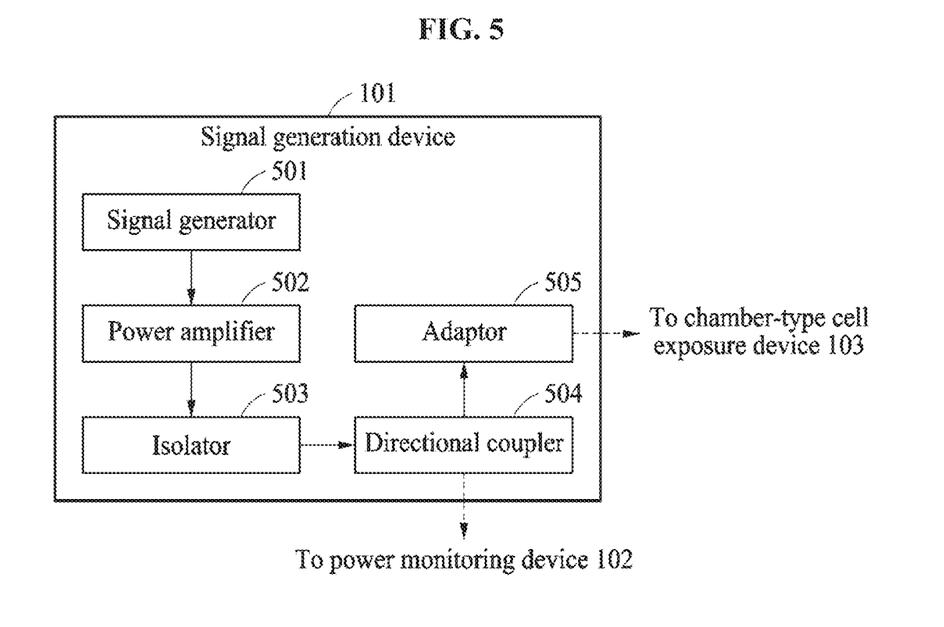
FIG. 5 is a diagram illustrating an example of a signal generation device according to an example embodiment.

FIG. 5 is a diagram illustrating an example of a signal generation device according to an example embodiment.

Referring to FIG. 5, the signal generation device 101 may generate an electromagnetic field in a short wavelength, such as, for example, a millimeter wave band, to be radiated to a cell container in order to conduct a cell experiment. The signal generation device 101 includes a signal generator 501, a power amplifier 502, an isolator 503, a directional coupler 504, and an adaptor 505.

The signal generator 501 may be a source of generating an electromagnetic field.

The power amplifier 502 may amplify the electromagnetic field generated from the signal generator 501. In detail, the power amplifier 502 may amplify power to compensate for a radiation efficiency based on exposure in the chamber-type cell exposure device 103 from a uniform field controller to an area in which the electromagnetic field is exhibited. Herein, the power amplifier 502 may receive an unnecessarily amplified reflected signal from the directional coupler 504 due to mismatching between components. Thus, the power amplifier 502 may include the isolator 503 to prevent the unnecessarily amplified reflected signal from entering the chamber-type cell exposure device 103. That is, in preparation of when the unnecessarily amplified reflected signal is input, the power amplifier 502 may include the isolator 503 as a safety device to turn it off when a reflection level of the reflected signal exceeds a predetermined value.

The isolator 503 may perform filtering on the electromagnetic field amplified by the power amplifier 502. In detail, when there is an undesired reflected and returning component in a signal with a strength of the electromagnetic field amplified by the power amplifier 502, the isolator 503 may perform dual safety functions of removing the undesired component and preventing the power amplifier 502 from failing.

The directional coupler 504 may measure the reflection level of the reflected signal of the electromagnetic field amplified by the power amplifier 502 and determine a threshold value of the measured reflection level. That is, the directional coupler 504 may extract power by the reflected signal of the electromagnetic field, and transfer the extracted power to the power monitoring device 102. The directional coupler 504 may transfer, to the power monitoring device 102, the power by the reflected signal of the electromagnetic field such that the power monitoring device 102 verifies whether a signal output required for an exposure experiment of the chamber-type cell exposure device 103 is generated.

The adaptor 505 may be used to match waveguide terminals for an input portion of the uniform field controller provided in the chamber-type cell exposure device 103 to feed the electromagnetic field to the chamber-type cell exposure device 103 and for an output portion of the directional coupler 504.

Figure 6:
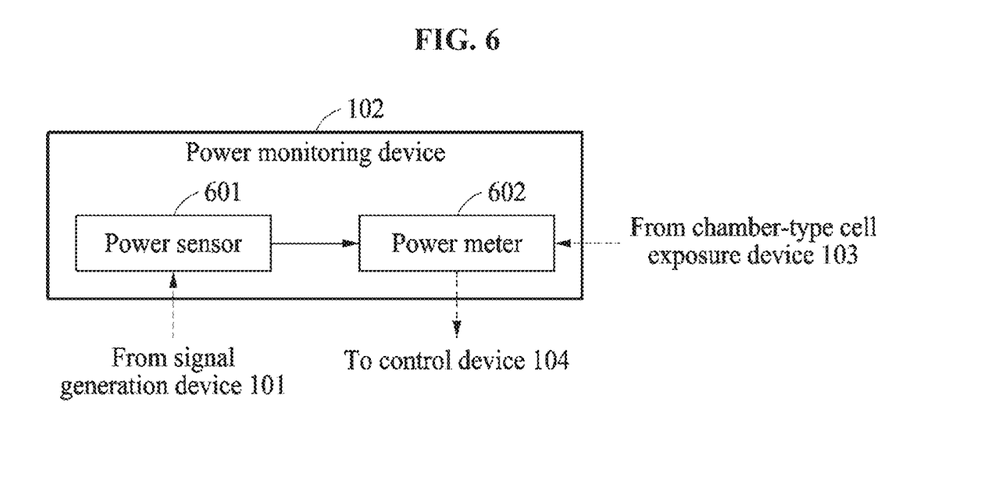
FIG. 6 is a diagram illustrating an example of a power monitoring device according to an example embodiment.

FIG. 6 is a diagram illustrating an example of a power monitoring device according to an example embodiment.

Referring to FIG. 6, the power monitoring device 102 may monitor power of an electromagnetic field. That is, the power monitoring device 102 may receive power of an electromagnetic field generated from the signal generation device 101, and verify whether the in vitro exposure system 100 operates normally and whether a desired level of power is generated for the chamber-type cell exposure device 103 to operate. The power monitoring to device 102 includes a power sensor 601 and a power meter 602.

The power sensor 601 may sense a certain level of power combined from a directional coupler of the signal generation device 101, and may thus sense amplified power through the directional coupler.

The power meter 602 may indicate a power value of the power sensed from the directional coupler, and indicate a power value measured from a planar scan probe of the chamber-type cell exposure device 103. That is, the power meter 602 may indicate both the power value of the directional coupler and the power value of the planar scan probe, and verify an exposure efficiency of the electromagnetic field being radiated to the chamber-type cell exposure device 103.

The power meter 602 may be embodied by a dual channel, and transfer the power values to the control device 104 such that the power values are indicated along with other parameters and measured values of the chamber-type cell exposure device 103.

Figure 7:
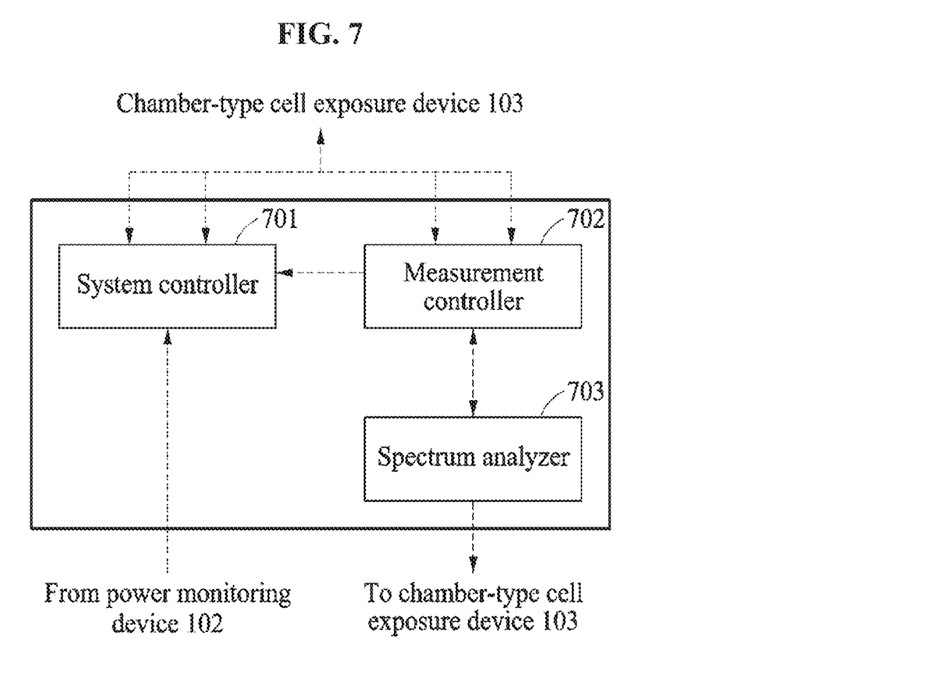
FIG. 7 is a diagram illustrating an example of a control device according to an example embodiment.

FIG. 7 is a diagram illustrating an example of a control device according to an example embodiment.

Referring to FIG. 7, the control device 104 may control an operation of the chamber-type cell exposure device 103. The control device 104 includes a system controller 701, a measurement controller 702, and a spectrum analyzer 703.

The system controller 701 may control a temperature sensor and an air-cooling ventilation controller of the chamber-type cell exposure device 103 through a control signal, indicate the control signal, and control an internal temperature of the chamber-type cell exposure device 103 not to increase to maintain an optimal temperature of the chamber-type cell exposure device 103. The system controller 701 may maintain the optimal temperature, and receive various power values from a power meter of the power monitoring device 102 and process the received power values such that the power values are indicated. In addition, the system controller 701 may monitor an output and warn of an abnormal operation in case of a prolonged cell exposure.

The measurement controller 702 may control positions of a planar scan probe and a position controller of the chamber-type cell exposure device 103, and transfer control information to the system controller 701 for monitoring.

The spectrum analyzer 703 may transmit an electromagnetic signal to operate the planar scan probe of the chamber-type cell exposure device 103 to feed power thereto, and simultaneously measure a strength of a sensed electromagnetic field. Herein, the spectrum analyzer 703 may be remotely controlled by the measurement controller 702 and related information may be verified through the system controller 701.

In addition, when a phase of an electromagnetic field also needs to be measured, the spectrum analyzer 703 may be replaced with a vector network analyzer of which one port replaces a position of the planar scan probe of the chamber-type cell exposure device 103 and another port replaces a position of a signal generator of the signal generation device 101, and that may remove an amplification factor of a power amplifier of the signal generation device 101 and apply a signal to a uniform field controller to measure a phase difference. However, the vector network analyzer may not permanently perform a function of generating an electromagnetic signal because only a measured input signal of the vector network analyzer may not replace a generated signal level of the signal generation device 101.

According to example embodiments described herein, an in vitro exposure system using a chamber-type cell exposure device may observe a result of a mechanism of a more effective cell experiment based on an increase in experimental cell group and control cell group by using experimental containers having a same amount of exposure to an electromagnetic field in a broader uniform field area.

According to example embodiments described herein, a chamber-type cell exposure device may use a temperature-controllable air-conditioning ventilation system to maintain an optimal temperature needed for a result of in vitro cell exposure in the chamber-type cell exposure device and to effectively control an increase in temperature.

According to example embodiments described herein, a chamber-type cell exposure device may use a planar scan probe configured to verify a flatness of a uniform field area, monitor an exposure level, and determine a distortion level of a reflected signal, in order to facilitate evaluation of characteristics of an electromagnetic field.

The components described in the example embodiments of the present disclosure may be achieved by hardware components including at least one of a digital signal processor (DSP), a processor, a controller, an application specific integrated circuit (ASIC), a programmable logic element such as a field programmable gate array (FPGA), other electronic devices, and combinations thereof. At least some of the functions or the processes described in the example embodiments of the present disclosure may be achieved by software, and the software may be recorded on a recording medium. The components, the functions, and the processes described in the example embodiments of the present disclosure may be achieved by a combination of hardware and software.

The processing device described herein may be implemented using hardware components, software components, and/or a combination thereof. For example, the processing device and the component described herein may be implemented using one or more general-purpose or special purpose computers, such as, for example, a processor, a controller and an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or to multiple types of processing elements. For example, a processing device may include multiple processors or a processor and a controller. In addition, different processing configurations are possible, such as parallel processors.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A chamber-type cell exposure device, comprising:
   a uniform field controller configured to radiate an electromagnetic field to a uniform field area formed around a position of a cell container arranged in the chamber-type cell exposure device;
   a temperature sensor configured to sense an internal temperature of the chamber-type cell exposure device that increases by the electromagnetic field radiated to the uniform field area;
   an air-cooling ventilation controller configured to control an air flow by adjusting an internal ventilation speed of the chamber-type cell exposure device based on the internal temperature sensed by the temperature sensor;
   a detachable support configured to adjust a position of the cell container to be arranged in the uniform field area;
   a planar scan probe configured to monitor a flatness and an exposure efficiency of the electromagnetic field radiated from the uniform field controller based on an amount of the electromagnetic field exposed to the uniform field area; and
   a position controller configured to triaxially control a position of the planar scan probe.

2. The chamber-type cell exposure device of claim 1, wherein the uniform field controller comprises:
- an antenna configured to radiate the electromagnetic field; and
- at least one lens configured to form a wavefront of the electromagnetic field.

3. The chamber-type cell exposure device of claim 1, wherein the uniform field controller is further configured to radiate the electromagnetic field to the uniform field area using the flatness determined by a strength of the electromagnetic field in the uniform field area in which the cell container is arranged and a phase of a wavefront of the electromagnetic field.

4. The chamber-type cell exposure device of claim 1, wherein the cell container has an electromagnetic field absorptance that varies based on a direction of the electromagnetic field radiated from the uniform field controller.

5. The chamber-type cell exposure device of claim 1, wherein the detachable support is at a height adjusted to allow the cell container to be arranged in an area with an identical exposure intensity and an identical phase of the electromagnetic field based on a uniformity of the electromagnetic field in the uniform field area.

6. The chamber-type cell exposure device of claim 1, wherein the detachable support is provided in a form that prevents a scattering distortion of the electromagnetic field radiated from the uniform field controller.

7. The chamber-type cell exposure device of claim 1, wherein the planar scan probe is arranged in the chamber-type cell exposure device in a direction that is 90 degrees)(° of rotation different from a main polarized direction of the electromagnetic field radiated from the uniform field controller.

8. The chamber-type cell exposure device of claim 7, wherein the planar scan probe is further configured to measure a distortion of the electromagnetic field by a signal reflected from a wave absorber of the chamber-type cell exposure device at a position at which the planar scan probe is arranged in the chamber-type cell exposure device, and to measure the amount of the electromagnetic field exposed based on the measured distortion of the electromagnetic field.

9. The chamber-type cell exposure device of claim 8, wherein the planar scan probe is further configured to determine a characteristic of a wavefront of the electromagnetic field with an identical exposure intensity and an identical phase of the electromagnetic field based on the flatness and the exposure efficiency of the electromagnetic field.

* * * * *